US008465782B2

(12) United States Patent
Bukowski et al.

(10) Patent No.: US 8,465,782 B2
(45) Date of Patent: Jun. 18, 2013

(54) METHODS AND MATERIALS FOR REDUCING RISK OF COLD AND/OR FLU (75) Inventors: Jack F. Bukowski, Marboro, MA (US); Jeffrey Walters, Winter Park, FL (US)

(73) Assignee: Immune Guard, LLC, Ft. Pierce, FL (US)

( * ) Notice: Subject to any disclaimer, the term of this patent is extended or adjusted under 35 U.S.C. 154(b) by 84 days.

(21) Appl. No.: 11/672,542

(22) Filed: Feb. 8, 2007

(65) Prior Publication Data
US 2008/0075765 A1 Mar. 27, 2008

Related U.S. Application Data (60) Provisional application No. 60/826,451, filed on Sep. 21, 2006.

(51) Int. Cl.
*A61K 36/82* (2006.01)
*A61K 9/48* (2006.01)

(52) U.S. Cl.
USPC .......................................... 424/729; 424/451

(58) Field of Classification Search
None
See application file for complete search history.

(56) References Cited

U.S. PATENT DOCUMENTS

| 5,137,922 A * | 8/1992 | Shimamura et al. ........... 514/731 |
| 2004/0047921 A1 | 3/2004 | Simmons et al. |
| 2004/0053858 A1 * | 3/2004 | Berg ............................... 514/27 |
| 2005/0090511 A1 * | 4/2005 | Shibahara ................. 514/263.31 |
| 2005/0287278 A1 * | 12/2005 | Quan et al. ..................... 426/597 |
| 2006/0018975 A1 | 1/2006 | Talbott |

FOREIGN PATENT DOCUMENTS

| JP | 56095182 A * | 8/1981 |
| JP | 2000152771 A * | 6/2000 |

OTHER PUBLICATIONS

Kiefer. "All about Supplements. Theanine: An Amino Acid from Tea has Numerous Health-Protecting Effects". Le Magazine. Aug. 2005.*
Beckman. Pharmacology: The Nature Action and Use of Drugs, Second Edition. W.B Saunders Company: Philadelpha and London, 1981. Chapter 6: Factors Affecting Drug Administration, pp. 38 and 39.*
University of Maryland: green tea. Sep. 30, 2005 [Retrieved from the Internet on: Feb. 14, 2009]. Retrieved from: <http://www.umm.edu/altmed/articles/green-tea-000255.htm>.*
Theanine. Internet Archive Date: Feb. 20, 2006 [Retrieved from the Internet on: Jun. 5, 2010]. Retrieved from: <http://web.archive.org/web/20060220211758/http://www.vitamins-supplements.org/amino-acids/theanine.php>.*
Kamath, A.B., "Anigens in Tea-Beverage Prime Human Vgamma2Vdelta2 T Cells in vitro and in vivo for Memory and Nonmemory Antibacterial Cytokine Responses", PNAS, May 2003, vol. 100, No. 10, pp. 6009-6014.
Hoq, M.M., "Role of gamma delta TCR Lymphocytes in the Augmented Resistance of Trehalose 6,6-DimycolateTreated mice to Influenza Virus Infection" Journal of General Virology, Jul. 1997, vol. 78, Part 7, pp. 1597-1603.
Bukowski, Jack F., "Is the increase in [gamma][delta] T cell priming by dietary alkylamines sufficient to prevent cancer? What other components of the diet prime [gamma] [delta] T cells?", Journal of Nutrition, Dec. 2005, vol. 135, No. 12, p. 2911S.
Bukowski, Jack F. et al, "Human gamma delta T cells recognize alkylamines derived from microbes, edible plants, and tea: implication for innate immunity", Immunity, Cell Press, Jul. 1999, vol. 11, No. 1, pp. 57-65.
Chow, H-H Sherry et al, "Phase I pharmacokinetic study of tea polyphenols following single dose administration of epigallocatechin gallate and Polyphenon E":, Cancer Epidemiology, Biomarkers and Prevention, Jan. 2001, vol. 10, No. 1, pp. 53-58.
Song et al., "Antiviral effect of catechins in green tea on influenza virus", Antiviral Research, Elsevier BV, Nov. 2005, vol. 68, No. 2, pp. 66-74.
Nakayama, M. et al., "Inhibition of the infectivity of influenza virus by tea polyphenols", Antiviral Research, Elsevier BV, Aug. 1993, vol. 21, No. 4, pp. 289-299.
Yam, T.S. et al. "Microbiological Activity of Whole and Fractioned Crude Extracts of Tea (*Camellia Sinesis*), and of Tea Components", FEMS Microbiology Letters, Blackwell Publishing, Amsterdam, NL, Jan. 1997, vol. 152, pp. 169-174.
Yamada, H. et al., "Gargling with tea catechin extracts for the prevention of influenza infection in elderly nursing home residents: A prospective clinical study", Journal of Alternative and Complementary Medicine, Mary Ann Liebert, New York, NY, Sep. 2006, vol. 12, No. 7, pp. 669-672.
Singh, Jasawant et al , "Immunomodulatory Activity of Tea", Protective Effects of Tea on Human Health, CABI International, Jan. 2006, pp. 34-44.

* cited by examiner

*Primary Examiner* — Amy L Clark
(74) *Attorney, Agent, or Firm* — Timothy H. Van Dyke; Beusse, Wolter, Sanks, Mora & Maire, P.A.

(57) ABSTRACT

Disclosed herein are compositions comprising tea derived components which are useful in reducing the incidence of cold and/or flu in a subject. Specifically exemplified herein are compositions comprising predetermined amounts of L-theanine and EGCG, and methods of using same.

6 Claims, 4 Drawing Sheets

METHODS AND MATERIALS FOR REDUCING RISK OF COLD AND/OR FLU

CROSS-REFERENCE TO RELATED APPLICATION

This application is related to U.S. Provisional Patent Application 60/826,451; filed Sep. 21, 2006 to which priority is claimed under 35 USC §119.

INTRODUCTION

For centuries, tea beverage has been linked to good health. Most studies have been observational, showing benefit in cardiovascular, anti-aging, neurodegenerative, anti-cancer, and bone areas [1-3]. There are numerous other studies consistent with no health benefits [4,5]. These studies, both positive and negative, are fraught with confounding variables that are inherent in observational studies employing free-living human beings as subjects. Such studies are further complicated by the nature of tea beverage. There are hundreds of varieties of the tea species, Camellia sinensis, and numerous ways to process tea that can lead to different components in a cup of tea [6,7]. Storing and brewing methods lead to further variability that is difficult to standardize. Another obvious source of conflict is that there is no general agreement on what quantity constitutes a cup of tea. Thus, it is not surprising that the results of many published trials conflict with one another.

Whereas most clinical tea research has focused on cardiac and cancer outcomes, there are no available clinical human data on prevention of cold and flu symptoms. These symptoms are the most common afflictions in humans, resulting in misery, loss of productivity, and absence from work and school [7]. Further, recent studies that call in to question the efficacy of zinc-based nasal sprays and lozenges [8], and Echinacea [9] make new research into cold and flu more important. Undoubtedly, there has been a long unmet need for a cold and flu preventive therapy that is safe and effective. Any advancement in developing a cold and/or flu preventive therapeutic product, either a pharmaceutical type product or natural product, would provide a dramatic benefit to the millions of people who suffer from colds and flu each year.

SUMMARY

The subject invention is based on the inventors surprising discovery that administration of composition containing standardized amounts of certain tea components, namely L-theanine and EGCG, enhances systemic immunity, and reduces the risk of onset of cold and flu symptoms in humans. Through a randomized, double-blind, placebo-controlled interventional study using compositions containing these key tea components (Camellia sinensis composition; CSC) with a primary endpoint of reduction in the number of subjects who developed cold and flu symptoms, the inventors have discovered that L-theanine and EGCG work together to generate surprising, unexpected, results of reducing the risk of cold and flu, and reducing the severity of symptoms of subject who contract colds and/or flu. The inventors present herein results showing that CSC reduces by about one third the number of subjects who develop cold and flu symptoms, while enhancing γδ T cell proliferation and IFN-γ secretion in response to microbial antigen.

BRIEF DESCRIPTION OF THE DRAWINGS

FIG. 4. Percentage of subject having individual symptoms. One of 56 (1.79%) CSF subjects had diarrhea; 3/55 (5.45%) placebo subjects had diarrhea (67.1% difference). Three of 56 (5.35%) CSF subjects had fever; 7/55 (12.7%) placebo subjects had fever (57.8% difference). Sixteen of 56 (28.6%) CSF subjects had sore throat; 25/55 (45.4%) placebo subjects had sore throat (37.0% difference). Fourteen of 56 (23.2%) CSF subjects had headache; 15/55 (27.2%) placebo subjects had headache (1.47% difference). Two of 56 (3.57%) CSF subjects had nausea; 4/55 (7.27%) placebo subjects had nausea (50.9% difference). Eleven of 56 (19.6%) CSF subjects had cough; 16/55 (29.1%) placebo subjects had cough (32.6% difference). Twenty of 56 (35.7%) CSF subject had runny nose; (29/56) (51.8%) placebo subjects had runny nose (31.1% difference). Nineteen of 56 (33.9%) CSF subjects had stuffy nose; 21/55 (38.2%) placebo subjects had stuffy nose (11.2% difference).

DETAILED DESCRIPTION

L-theanine, abundant in tea, is catabolized in the body to yield ethylamine, a gamma delta T cell antigen, which appears in the blood of rats given L-theanine, and has been shown to appear in the urine of tea drinkers. Tea extraction procedures normally exclude amino acids, including L-theanine. Compositions taught herein are unique in that they intentionally combine L-theanine and an EGCG in enriched amounts.

The EGCG composition is procured from tea and comprises between 10-100 percent EGCG, by weight. In optimal embodiments, the EGCG comprises at least 40 to 50 percent EGCG, by weight. It is known that EGCG procured from tea can contain caffeine. U.S. Pat. No. 7,012,149 is cited for background on procuring EGCG containing composition. Also commercially available products such as SUNPHENON® line of products from Taiyo International, Minneapolis, Minn. offer EGCG compositions may be used in accordance with the teachings herein.

In preferred embodiments caffeine is reduced or eliminated from the EGCG composition either before or after procurement of the EGCG composition. The inventors have found that reducing the caffeine amount provides a novel composition with increased compliance. Caffeine intake can cause a number of adverse side effects, including, but not limited to, excitability in children, constipation, nervousness, dizziness, hypertension, and arythmias. For certain embodiments, the inventors have realized that compositions may be particularly marketed to schools for use in beverages and food served to students. Schools can be a primary source epicenter of virus origination and distribution. The administration of compositions taught herein will serve to reduce or slow the spread of microbial infections. A composition containing caffeine would not be appropriate for such application.

The procurement of L-theanine is separate from tea polyphenols. Accordingly, an L-theanine composition is obtained from tea where the L-theanine composition comprises between 10-100 percent L-theanine. This L-theanine composition may be admixed with the EGCG containing tea polyphenol composition. See U.S. Pat. No. 6,831,103 for background on procurement of L-theanine.

Theanine may be a glutamic acid derivative (γ-glutamylethylamide), which is an amino acid component naturally contained largely in tea-leaves. Methods for preparing theanine used in the present invention may include, for instance, a method of extracting from tea-leaves; an organic synthesis method [Chem. Pharm. Bull, 19(7), 1301-1307 (1971)]; a method of treating a mixture of glutamine and ethylamine with glutaminase (Japanese Unexamined Patent Publication No. Hei 7-55154); a method comprising culturing cultured cells of tea in a medium containing ethylamine, thereby achieving growth promotion of the cultured cells while increasing the cumulative amount of theanine in the cultured cells (Japanese Patent Laid-Open No. Hei 5-123166); modification methods in which ethylamine is substituted by an ethylamine derivative such as ethylamine hydrochloride in the methods disclosed in Japanese Unexamined Patent Publication No. Hei 7-55154 or Japanese Patent Laid-Open No. Hei 5-123166; and the like, and any of the methods may be used. The above-mentioned "tea-leaves" include green tea-leaves, oolong tea-leaves, black tea-leaves, and the like.

Theanine can be used as any of L-theanine, D-theanine and DL-theanine. Among them, the L-form is preferred in the present invention, because the L-form is approved as a food additive, and is economically utilizable. In addition, theanine used in the present invention may be in any forms, such as purified products, crudely purified products and extracts. Also, a commercially available product [SUNTHEANINE (registered trade mark), manufactured by Taiyo Kagaku Co., Ltd.] may be used.

According to one embodiment, the invention pertains to a method of reducing the incidence of colds and/or flu comprising orally administering a composition comprising L-theanine and EGCG, wherein said composition is administered according to a dosage amounting to at least 25 mg of L-theanine and 25 mg EGCG per day. In a specific embodiment at least 200 mg of L-theanine is administered per day. In a further embodiment at least 150 mg of L-theanine is co-administered with at least 125 mg of EGCG per day. In a particular embodiment, between 180 to 220 mg of L-theanine and between 180 to 220 mg of EGCG is administered per day. In alternative embodiments, the daily amount of EGCG that is used to combine with L-theanine is from about 200 mg to 450 mg. In specific embodiment EGCG is provided at up to 800 mg of 45 percent EGCG composition.

According to another embodiment, the invention pertains to a capsule or tablet or liquid suspension comprising a combination of L-theanine and EGCG, wherein the capsule or table comprises between 10 percent to 100 percent, by weight, L-theanine and between 10 percent to 100 percent, by weight EGCG. In a specific embodiment, the capsule or tablet comprises between 15 percent to 65 percent L-theanine and 15 percent to 65 percent EGCG. In a further embodiment, the capsule or tablet or suspension comprises between 30 percent to 60 percent, by weight, tea polyphenols. In a specific embodiment, the capsule or table or suspension is decaffeinated. In an alternative embodiment, the capsule or tablet may contain sulphoraphane (from 5-50 mg per day).

The tablet or capsule may be, but is not limited to, from 10 to 500 mg total weight. In specific embodiments, the capsules are 25, 50, 75, 100, 125, 150, 175, 200, 225, 250, 275, 300, 325, 350, 375, 400, 425, 450, 475, or 500 mg, total individual weight.

According to another embodiment, the invention pertains to reducing the severity of symptoms of cold and/or flu comprising orally administering a composition comprising L-theanine and EGCG, wherein said composition is administered according to a dosage amounting to at least 25 mg of L-theanine a day. In a specific embodiment at least 100 mg of L-theanine is administered per day. In a further embodiment at least 115 mg of L-theanine is co-administered with at least 100 mg of EGCG per day. In a particular embodiment, between 150 to 600 mg. of L-theanine and between 150 to 600 mg of EGCG is administered per day.

According to another embodiment, the invention pertains to reducing the severity of symptoms of cold and/or flu comprising orally administering a beverage comprising water, flavoring, EGCG composition, and L-theanine, wherein said beverage is administered according to a dosage amounting to at least 25 mg of L-theanine a day and at least 25 mg of EGCG composition a day. In a specific embodiment at least 100 mg of L-theanine is administered per day. In a further embodiment at least 120 mg of L-theanine is co-administered with at least 125 mg of EGCG per day. In a specific embodiment, between 150 to 600 mg. of L-theanine and between 150 to 600 mg of EGCG is administered per day.

According to another embodiment, the subject invention pertains to a method of enhancing immune function by $\gamma\delta$ T cells in a subject comprising orally administering a therapeutically effective amount of a composition comprising L-theanine and EGCG, wherein said composition is administered according to a dosage amounting to at least 25 mg of L-theanine and at least 25 mg of EGCG per day. In a more specific embodiment, composition comprises an admixture of an L-theanine composition comprising at least 10-100 percent L-theanine and a decaffeinated tea polyphenol composition comprising at least 10-100 percent EGCG For certain method embodiments, the dosage of L-theanine is at least 25 mg per day. The dosage of L-theanine is typically between 25-600 mg of L-theanine a day, but may be higher than 600 mg. In certain embodiments, the dosage of L-theanine is or about 25, 50, 75, 100, 125, 150, 160, 170, 180, 190, 200, 210, 220, 230, 240, 260, 280, 300, 320, 340, 360, 380, 400, 420, 440, 460, 480, 500, 520, 540, 560, 580 or 600 mg of L-theanine a day. In a specific embodiment, the dosage is such that about 200 mg L-theanine is provided per day. The dosage of EGCG is at least 25 mg per day. The dosage of EGCG is typically between 25-600 mg of EGCG a day. In certain embodiments, the dosage of L-theanine is or about 25, 50, 75, 100, 125, 150, 160, 170, 180, 190, 200, 210, 220, 230, 240, 260, 280, 300, 320, 340, 360, 380, 400, 420, 440, 460, 480, 500, 520, 540, 560, 580 or 600 mg of L-theanine a day. In a specific embodiment, the dosage is such that about 200 mg L-theanine is provided per day.

In another embodiment, the subject invention is directed a composition comprising an admixture of an L-theanine composition and a decaffeinated tea polyphenol composition, wherein said L-theanine composition comprises at least 50 percent L-theanine and said decaffeinated tea polyphenol composition comprises at least 30 percent EGCG, wherein said L-theanine composition and tea polyphenol composition are present in a ratio of 2:1, 1.9:1, 1.8:1, 1.7:1, 1.6:1, 1.5:1, 1.4:1, 1.3:1, 1.2:1, 1:1, 1:1.1, 1:1.2, 1:1.3, 1:1.4, 1:1.5, 1:1.6, 1:1.7, 1:1.8, 1:1.9, 1:2, or 1:3 respective to each other. In a related embodiment, the composition is used as a food additive. In a specific embodiment, the composition comprises between 10 percent to 80 percent, by weight, L-theanine and between 10 percent to 80 percent, by weight EGCG. In a specific embodiment, the capsule or tablet comprises between 15 percent to 65 percent L-theanine and 15 percent to 65 percent EGCG. In a more specific embodiment, the composition comprises between 20 percent to 40 percent L-theanine and 20 percent to 40 percent EGCG.

In yet another embodiment, the subject invention pertains to a food product comprising a therapeutically effective amount of L-theanine and EGCG. In a specific embodiment, the invention relates to a food product comprising at least 25 mg of a L-theanine and tea polyphenol composition, such as, but not limited to, the composition described in the preceding paragraph. Examples of food products may include, but are not limited to, energy bars, sauces, salad dressings, frozen dinners, chips, canned soups, yogurt, cereals, bread, flour and grains. In an alternative but related embodiment, the subject invention pertains to a packaged food product having a total weight of between 25 mg to 50 kg. The packaged food product comprises at least 0.1 percent by weight L-theanine and at least 0.1 percent by weight EGCG. In a specific embodiment, the food product comprises between about 0.1-10 percent, by weight, L-theanine and between about 0.1 to 10 percent, by weight, EGCG. In other embodiments, the amount of L-theanine and EGCG are at least 25 mg per serving.

Not to be bound by any particular mechanistic theory, it is the belief of the inventors that the unexpected antiviral effects of certain embodiments is due to a one-way synergy between L-theanine and EGCG. In particular, the inventors believe that there is one-way synergy, in two dimensions: in the first dimension, the L-theanine catabolite ethylamine binds to $\gamma\delta$ T cells to prime them for activation (proliferation and IFN-$\gamma$ secretion) by cold and flu viruses and IL-12. EGCG serves to enhance the secretion of IL-12, which is essential for $\gamma\delta$ T cell activation and protection against cold and flu (refs 18 and 20). The IFN-$\gamma$ is what acts against viruses. However, as an unwanted side effect, this IFN-$\gamma$ acts on macrophages, causing the release of oxygen free radicals, and cytokines such as IL-1 and TNF-$\alpha$ that are toxic to cells of the lung, nose, and throat. These toxicities create symptoms of cold and flu. In the second dimension, EGCG mimimizes this damage created by L-theanine's action on $\gamma\delta$ T cells by decreasing the synthesis of these toxins and also protecting the lung, nose, and throat cells against the damaging effects of these toxins. (REFS 20, 22-25)

In certain embodiments, the composition will generally be used in an amount effective to achieve the intended purpose. For use to treat or prevent the above diseases or disorders the CSC is administered or applied in a therapeutically effective amount.

The amount of a L-theanine and EGCG, and/or CSC including such compounds, that will be effective in the treatment of a particular disorder or condition disclosed herein will depend on the nature of the disorder or condition, and can be determined by standard clinical techniques known in the art and by doctors skilled in treating or preventing a particular disease or disorder. In addition, in vitro or in vivo assays may optionally be employed to help identify optimal dosage ranges. The amount of a compound of the invention and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a a single administration, by multiple applications or controlled release. In one embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are generally about 0.0001 mg to about 2000 mg of a compound of the invention per kilogram body weight. In one embodiment, the dosage range is between about 0.1 mg/kg to about 5 mg/kg. Dosage ranges may be readily determined by methods known to the artisan of ordinary skill. Effective doses may be extrapolated from dose-response curves derived from in vitro or animal model test systems. Such animal models and systems are well-known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred. The compounds of the invention may also be demonstrated to be effective and safe using animal model systems.

Preferably, a therapeutically effective dose of a compound of the invention and/or pharmaceutical composition thereof described herein will provide therapeutic benefit without causing substantial toxicity. Toxicity of compounds of the invention and/or pharmaceutical compositions thereof may be determined using standard pharmaceutical procedures and may be readily ascertained by the skilled artisan. The dose ratio between toxic and therapeutic effect is the therapeutic index. A compound of the invention and/or pharmaceutical composition thereof will preferably exhibit particularly high therapeutic indices in treating disease and disorders. The dosage of a compound of the invention and/or pharmaceutical composition thereof described herein will preferably be within a range of circulating concentrations that include an effective dose with little or no toxicity.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described.

Those skilled in the art of medicinal chemistry and pharmaceutical formulations will appreciate that other formulations can be devised for appropriate oral, parenteral or other administration. U.S. Pat. Nos. 6,821,532 and 7,157,493 are cited for general background of pharmaceutical formulations.

Example 1

EGCG/L-Theanine Formulation Embodiment

According to a specific embodiment, the invention pertains to a capsule comprising an admixture of or about 25-300 mg of an at least 95 percent L-theanine containing composition and of or about 50-400 mg of a decaffeinated tea polyphenol composition containing at least 45 percent EGCG. In a more specific embodiment, the subject invention pertains to a capsule comprising 300 mg of an admixture comprising 100 mg of a 98 percent L-theanine containing composition and 200 mg of a 50 percent EGCG containing tea polyphenol composition.

Example 2

Cold and/or Flu Treatment/Prevention Beverage

According to another embodiment, the invention pertains to an article of manufacture comprising a beverage comprising water, flavoring, EGCG composition, and L-theanine and a container in which the beverage is disposed. In certain embodiments, the container volume may be in the range of between 25 ml to 5000 ml. The article of manufacture comprises at least 25 mg of L-theanine and at least 25 mg of EGCG. In a preferred embodiment, the article of manufacture comprises at least 50 mg of L-theanine and at least 50 mg of EGCG. In a specific embodiment, the article of manufacture comprises at least 75 mg, 100 mg, 125 mg, 150 mg, 175 mg, 200 mg 225 mg or 250 mg of EGCG and at least 75 mg, 100 mg, 125 mg, 150 mg, 175 mg, 200 mg 225 mg or 250 mg mg of L-theanine. The EGCG composition is procured from tea and comprises between 10-100 percent EGCG, by weight. In optimal embodiments, the EGCG comprises at least 40 to 50 percent EGCG, by weight. It is known that EGCG procured from tea can contain caffeine. In preferred embodiments caffeine is reduced or eliminated from the EGCG composition either before or after procurement of the EGCG composition. The procurement of L-theanine is separate from tea polyphenols. Accordingly, an L-theanine composition is obtained from tea where the L-theanine composition comprises between 10-100 percent L-theanine. This is admixed with the EGCG containing tea polyphenol composition. Flavorings pertain to any substance that is used to modify, enhance or mask flavors. Flavors can include but are not limited to sweeteners, salts, flavor substances, acidulents. Sweetener includes both natural and artificial sweeteners. Sweeteners include, but are not limited to, sucralose, acesulfame potassium, aspartame, saccharin, sucrose, glucose, fructose, high fructose corn syrup, invert sugars, sugar alcohols including sorbitol, mannitol and mixtures thereof. As used herein, the term "acidulents" includes, but is not limited to, citric acid, lactic acid, malic acid, sodium citrate, potassium citrate. As used herein, the term "preservatives/antimicrobial agents" includes, but is not limited to sodium benzoate, potassium benzoate, benzoic acid, ethylparaben, methylparaben, propylparaben, sorbic acid.

Examples of beverages include, but are not limited to, fruit juice mixed with the L-theanine/EGCG composition, a "smoothie" (fruit juice and blended fruit) with L-theanine/EGCG composition provided therein, fitness drinks, such as GATORADE®, POWERADE®, etc. with composition provided therein, tea drinks with composition added therein, and sodas with composition added therein.

Example 3

Double Blind Placebo Study

Materials and Methods

Subjects. Healthy men (n=52) and women (n=72) between 21 and 70 (mean=29) years of age were recruited to participate in a 12-wk randomized, double-blind placebo controlled parallel study. Subjects were recruited from the University of Florida campus, and the Gainesville, Fla. community, during January of 2006. The University of Florida Institutional Review Board approved the study protocol, and informed written consent was obtained from each subject. Screening for the study occurred by telephone and/or personal interviews. Exclusion criteria consisted of the following: had not had a cold in the past two years; vegetarian diet; steroids; chemotherapy or other immune suppressing therapy within the last year; chronic antibiotics or other infectious disease preventative; chronic illness; recent surgery or illness; pregnant and/or lactating females. Also excluded were those who daily consumed: greater than one cup (250 mL) of tea; an average of seven or more servings of fruits and vegetables; herbal supplements, vitamins other than a multivitamin or vitamin D, or osteoporosis medicine or medications containing bisphosphonates, that are activators of γδ T cells [10]. The study was conducted from January through May of 2006. Participants were in contact with the enrolling research assistant by e-mail and telephone throughout the study, and returned to fill out an exit questionnaire upon study completion. Overall study compliance was monitored through the exit questionnaire and by enumeration of remaining capsules in returned bottles at the end of then study [11].

Study Protocol. The study was conducted from January through May of 2006, to coincide with normal cold and flu season. The CDC weekly report of influenza activity in Florida was as follows: January-March regional to widespread, March-April widespread to local activity, April-May local activity to sporadic.

Subjects were randomly assigned to supplement and placebo groups. Both subjects and investigators were blinded as to the treatments. Human Health Biotech Institute (Naples, Fla.) provided CSC and placebo capsules. The CSC was decaffeinated and comprised a mixture of L-theanine (Suntheanine®, standardized at 99%; Taiyo International, Minneapolis, Minn.), and epigallocatechin gallate (EGCG; Sunphenon®, Taiyo International, Minneapolis, Minn., standardized at 50%). The placebo capsules contained microcrystalline cellulose, dextrose, dicalcium phosphate, magnesium stearate, silicon dioxide, FD&C red #40, yellow #6, and blue #1. Each participant was given a bottle containing 180 capsules and was instructed to take 2 capsules every day (one in the morning and one in the evening, preferably with meals) for 12 weeks.

Subjects were given an illness log to record any cold and flu symptoms during the 12 week experimental period. Primary outcomes were defined as the number of subjects experiencing any symptoms, and the mean number of days they self-reported symptoms. The symptoms assessed were: runny nose, congested or stuffy nose, headache, cough, sore throat, fever, nausea/vomiting, and diarrhea. Subjects were also asked to report if they sought medical treatment and were prescribed any medications as a result of seeking treatment. The exit questionnaire included questions: to determine if subjects experienced any side effects and/or experienced any changes in feelings of stress or anxiety, or took any additional dietary supplements during the study. Finally, subjects were asked to report whether they thought they had taken the active or the placebo capsules.

Blood collection. Blood was obtained from fasting subjects on Days 0 (baseline), and 21. Blood was collected into one 10 mL sodium heparin tubes for peripheral blood mononuclear cell (PBMC) separation, and one 10 mL SST™ tube (Vacutainer, Becton Dickinson, Franklin Lakes, N.J.) for serum. Tubes for PBMC were maintained at room temperature (RT), while tubes for serum were kept at 4° C. All tubes were processed within 1 hr of blood collection. Blood cell separation and culture procedures were carried out under sterile conditions.

Serum collection and treatment. Serum was removed from SST™ tubes after centrifugation (100 g, 10 min, 4° C.) and frozen at −80° C.

Blood cell separation. Whole blood was diluted and placed on a gradient to separate PBMC. Briefly, 7 mL of whole, anti-coagulated blood (RT) was diluted 1:1 with 0.9% NaCl. Diluted blood (6 mL) was layered over 3 mL of Nycoprep 1-Step™ 1.077 (Axis-Shield, Oslo, Norway) and centrifuged (800 g, 20 min, 20° C.). The mononuclear cell layer was removed, washed twice with 10% FBS-RPMI 1640 (Cellgro; Mediatech, Herndon, Va.) complete (100 U/mL Penicillin; 100 μg/mL Streptomycin; 0.25 μg/mL Fungizone; 50 μg/mL Gentamycin; 2 mM l-glutamine; 25 mM HEPES) by centrifugation (400 g, 10 min, 4° C.). Individual cell pellets were resuspended in 2 mL RPMI 1640 complete, without serum, and counted on a Z-2 Coulter Counter (3.8μ setting for the 100 μm aperture tube, Beckman Coulter, Inc., Fullerton, Calif.).

Culture of peripheral blood mononuclear cells (PBMC) for γδ T-cell expansion and cytokine production. On Day 0, $1.0\times 10^6$ PBMC in 10% FBS-RPMI 1640 complete medium containing 50 μM 2-ME, were seeded into each of two wells of duplicate 24-well tissue culture plates (Costar, Corning, N.Y.). Ethylamine (1 mM/mL, Sigma) in the same medium was added to one set of wells on each plate, while the other set was mock treated with 1 mL medium. The plate was incubated in a humidified 5% $CO_2$ atmosphere at 37° C. On Day 1, cells and supernatant fluids from one plate were harvested and centrifuged (1500, 10 min, 4° C.). The supernatant fluids were removed and frozen at −80° C. for cytokine analysis, while the cell pellets were re-suspended in 0.1 mL PBS and 0.5 mL RNAlater™ (Ambion, Austin, Tex.) and frozen at −80° C. On Day 3, 30 U/mL of recombinant human IL-2 (BD Biosciences, San Diego, Calif.) were added to all wells of the remaining plate, which was incubated until Day 10 when cells were harvested. Total cell counts were obtained on a Coulter Counter (4.5μ setting) and dead cells enumerated via trypan blue exclusion on a hemocytometer, and cells processed for flow cytometry.

Flow cytometry. The ratio of αβ and γδ T-cells in PBMC suspensions and cultures was determined by flow cytometry, using cell surface markers for identification on Days 0 and 10 of culture.

Antibodies:

Phycoerythrin (PE)-conjugated anti-human $CD3^+$, and fluorescein isothiocyanate (FITC)-conjugated anti-human T-cell surface markers αβTCR and γδTCR (eBioscience, San Diego, Calif.) were used to stain PBMC.

Staining/Fixation:

PBMC in staining buffer (PBS+0.1% $NaN_3$+2% FBS) were stained on ice in the dark for 30 min, with PE anti-human $CD3^+$ antibody and one of the two FITC-conjugated TCR specific antibodies. Cells were washed (PBS+0.1% $NaN_3$) by centrifugation (1000 g, 10 min, 20° C.). Cells were fixed with 1% paraformaldehyde in PBS+0.1% $NaN_3$. Cells were analyzed within 24 hours on a FACScan (Becton-Dickinson, San Jose, Calif.). Data was analyzed using WinMDI Software (Scripps Institute, build 1301-19-2000). Data collected was from gated $CD3^+$ cells (events). Final data is reported as the mean percentage of cells expressing the specific cell surface marker, ± the standard deviation (SD).

Cytokine level determination in supernatants from cell proliferation Levels of human IFN-γ from PBMC culture supernatants were quantified using enzyme linked-immunosorbent assay (ELISA) kits, according to the manufacturer's directions (BD Biosciences Pharmingen, San Diego, Calif.). Human cytokine standards provided with each kit were used for a standard curve. Supernatants were analyzed undiluted for IFN-γ. Plates were read at 450 nm (with λ correction of 570 nm) on a SPECTRAmax 340PC plate reader (Molecular Devices, Menlo Park, Calif.). Cytokine concentrations were calculated as the mean value obtained for values within the range of the standard curve. The limits of detection of the cytokine ELISA kits were: IFNγ-300 pg/mL.

Statistical Analysis. For analysis describing the percentage of subjects experiencing symptoms, the two sample t test between percents was used. For analysis describing symptom days, the independent groups t test for means was used. Two-way ANOVA was used for γδ T cell proliferation studies and IFN-γ secretion.

Results

Study Subjects

One hundred and twenty-four subjects were enrolled in the study. Six subjects withdrew from the study (three CSC, and three placebo). Adverse events were mild, infrequent, and transient. Bloating, gastric upset, dizziness, skin rash, and constipation were reported, and were not different between experimental and control groups. Two subjects taking CSC withdrew with mild skin rashes. One subject said she thought the rash was related to a seafood allergy, and the other thought it might be from the capsule. Neither subject sought medical attention. Such food allergies for green tea have been described previously, mostly in tea factory workers, and the causative agent in green tea is EGCG [12]. However, other reports in the literature describe EGCG as beneficial for asthma and atopic dermatitis [13, 14].

One placebo subject withdrew due to an unrelated urinary tract infection. One placebo individual withdrew because traveling interfered. One placebo individual withdrew because he could not return. One placebo subject withdrew because he just stopped taking the capsules (Table 1). Five more subjects (two CSC and three placebo) were excluded from all data because they were less than 70% compliant. Two more subjects (one CSC and one placebo) were excluded when they reported in their logs that they were ill when the study began, which was an exclusion criterion. Fifty-six subjects in the supplement group and 55 subjects in the placebo group completed the study with 70% or greater compliance, and their data were included in all results and analyses.

Demographics

Average age, gender and BMI values did not differ between experimental and control groups. Subjects were adequately blinded, as there was no difference between CSC and placebo in the percentage of subjects who guessed which treatment to which they were assigned (Table 2).

Ingestion of *Camellia sinensis* Composition (CSC) Reduced the Number of Subjects Having Cold and Flu Symptoms.

Figure 1:
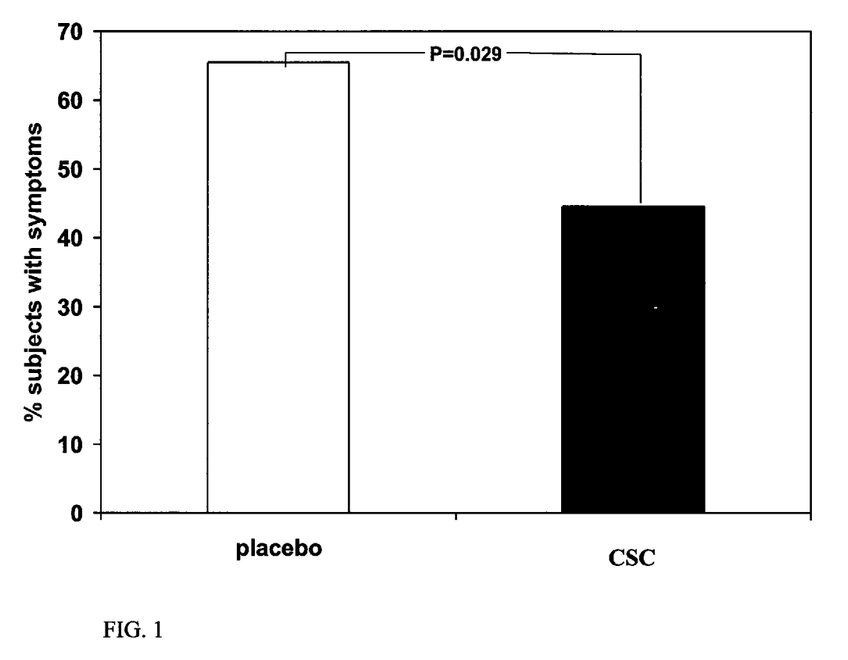
FIG. 1 Shows a graph representing the percentage of 56 CSC subjects and 55 placebo subjects who had at least one symptom during the 12-week study period.

Throughout the three month study, subjects were asked to keep an illness log to report daily cold and flu symptoms, including fever, runny nose, stuffy nose, sore throat, cough, headache, diarrhea, and nausea. Thirty-six of 55 (65.5%) placebo subjects, but only 25 of 56 (44.6%) CSC subjects had at least one symptom during the 12 week study. Thus, 31.9% fewer subjects taking CSC experienced cold and flu symptoms as compared to subjects taking placebo (P<0.029; FIG. 1).

Figure 2:
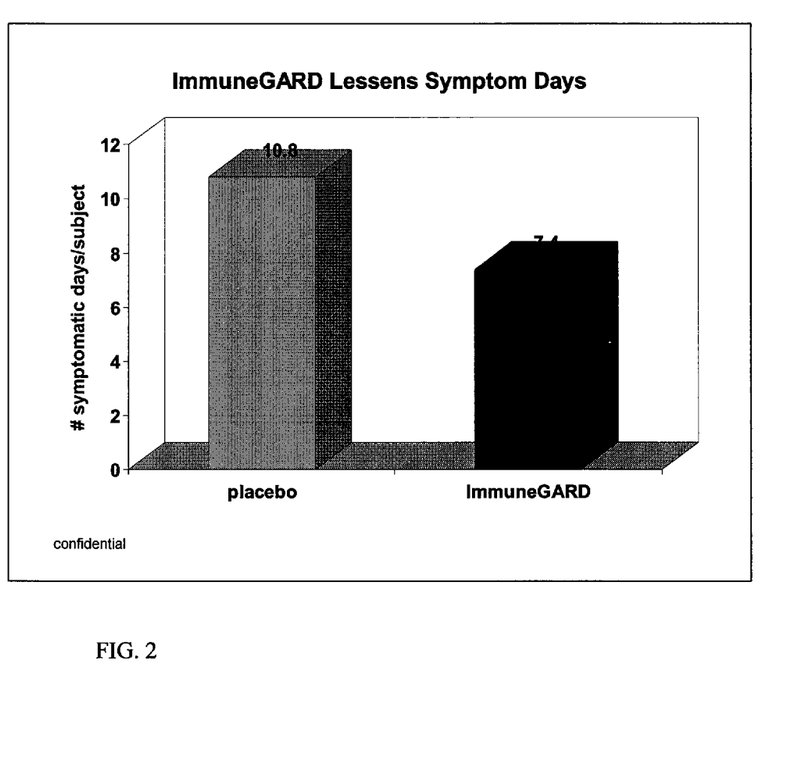
FIG. 2. Mean number of days each subject had cold and flu symptoms over the 12 week study period.
Figure 3:
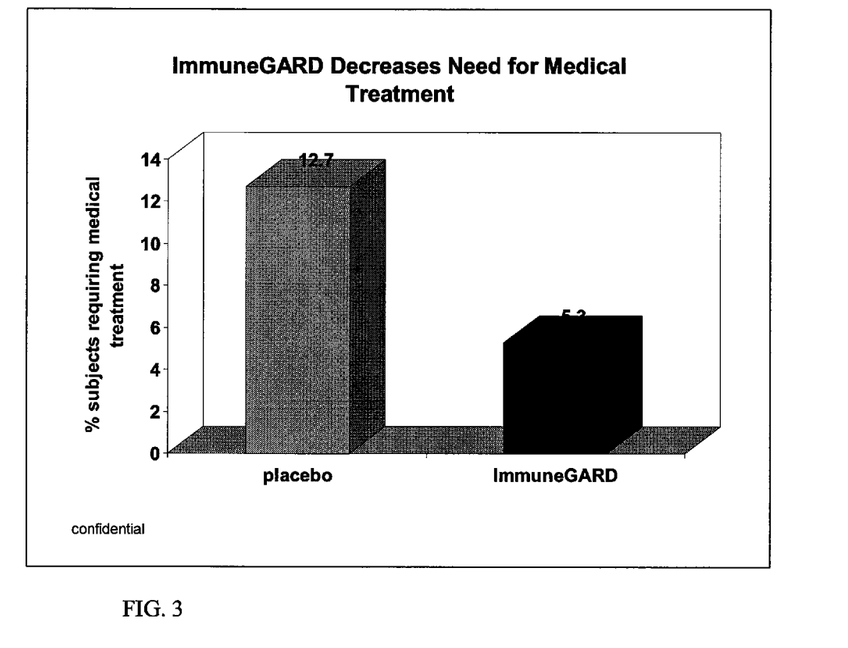
FIG. 3. Percentage of subjects seeking medical treatment.
Figure 4:
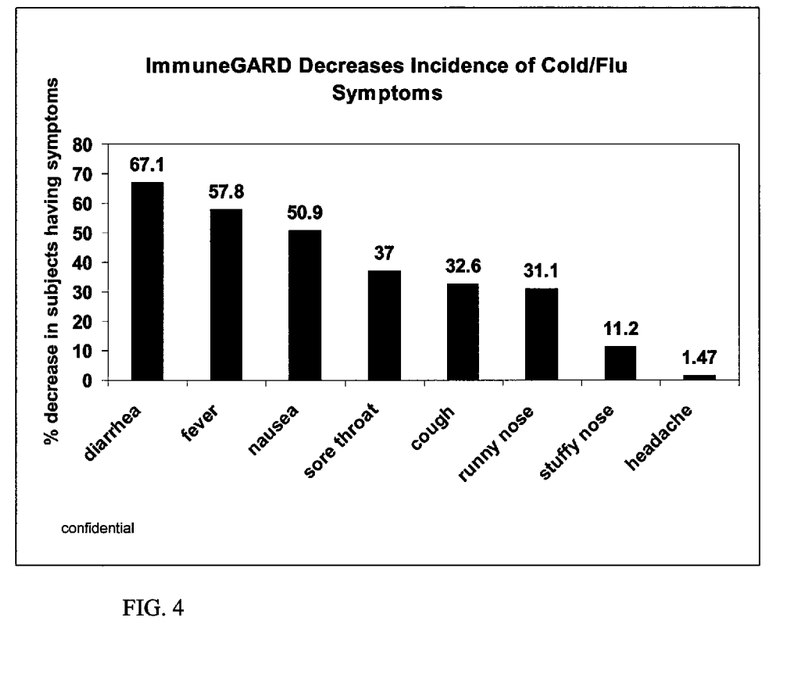

Fifty-six CSC subjects had a total of 412 symptom days (mean, 7.37+/−13.95), and 55 placebo subjects had a total of 595 symptom days (mean, 10.8+/−14.98). This represents a 30.2% reduction in the number of symptoms days for CSC subjects as compared to the placebo group (P<0.199; FIG. 2). Three of 56 (5.3%) CSC subjects, and six of 55 (12.7%) placebo subjects sought medical treatment (58.3% difference; P<0.175; FIG. 3). We analyzed the subjects in each group with regard to eight individual symptoms. There were 67.1, 57.8, 50.9, 37, 32.6, 31.1, 11.2, 1.47 percent fewer CSC subjects experiencing diarrhea, fever, nausea, sore throat, cough, runny nose, stuffy nose, and headache, respectively, as compared to placebo subjects, but differences within each individual symptom did not reach statistical significance (FIG. 4 and Table 5).

Taken together, these results show that CSC is effective in preventing cold and flu symptoms in this group of healthy volunteers. The data suggest that CSC may also decrease the duration of symptoms and the need for medical treatment.

Ingestion of CSC Enhanced Proliferation and IFN-γ Secretion by γδ T Cells.

Our previous study showed that PBMC taken from subjects who started drinking daily five to six cups of tea, containing L-theanine, for as little as one week secreted significantly more IFN-γ in response to γδ T cell antigens, as compared to before [20]. To determine if ingestion of CSC, containing L-theanine, could enhance IFN-γ production, we isolated PBMC taken from subjects three weeks after they started taking CSC or placebo, and cultured them for 24 hours with media alone, or with media containing ethylamine, which is a γδ T cell antigen that is a byproduct of L-theanine catabolism (Table 3). It is important to note that only γδ T cells respond to ethylamine [19, 15], and that CSC ingestion had no effect on IFN-γ secretion or T cell proliferation in response to a non-specific T cell mitogen, phytohemagglutinin. Also, absolute numbers of αβ T cells did not change when cultured in media alone, or with ethylamine (data not shown). PBMC from CSC placebo subjects secreted only 2.8 and 2.3 ng/mL IFN-γ, respectively. As expected, PBMC from placebo subjects secreted more IFN-γ in response to 5 mM ethylamine as compared to media alone (13.6 ng/mL). However PBMC from CSC subjects secreted 18.4 ng/mL IFN-γ in response to ethylamine. This response was 26% higher than that from placebo PMBC (P=0.046).

We established separate 10-day PBMC cultures from the subjects to assess by flow cytometry the proliferative responses of αβ and γδ T cells (Table 4). In the presence of ethylamine, γδ T cells from CSC subjects expanded to 28% of CD3+ cells, as compared to 20.3% from placebo subjects (P=0.017). Thus, CSC consumption was associated with a significant increase in the capacity of 76 T cells to secrete IFN-γ and to proliferate in response to antigenic challenge.

DISCUSSION

Fewer than 5% of Americans eat the nine servings per day of fruits and vegetables suggested by the latest USDA guidelines released in 2005 [16]. Only 20% of Americans drink any tea at all, while those who do only drink an average of one to two cups per day. Unfortunately, most health benefits from tea are associated with higher amounts of daily consumption [1]. Tea is a vegetable infusion, containing antioxidants and other beneficial nutrients such as L-theanine. Numerous observational studies suggest that tea drinking is beneficial to health, but negative studies have introduced controversy surrounding its health benefits. Though any two studies can yield different results, the conflict between negative and positive studies is likely due in large measure to the observational nature of the studies, and differences in tea preparations (see introduction). We have conducted a randomized, double blind placebo-controlled study using a *Camellia sinensis* composition (CSC) with defined amounts of L-theanine and EGCG that as closely as possible approximates the ingestion of 10 cups of green tea per day. The strength of this design lies in elimination of subject selection bias inherent in observational studies. Another strength is the elimination of the variability that can be associated with tea varieties and tea beverage preparations.

The results show that the ingestion of two capsules daily decreased by about a third the number of subjects who experienced cold and flu symptoms. Also seen were decreases in the number of days subjects had symptoms, the number of subjects who had specific cold and flu symptoms, and the number of subjects needing medical treatment. The CSC benefits seen were not related to sex, gender, race, or BMI. The magnitude of reduction of these symptoms in a preventive manner has enormous implications for public health.

In addition to its effect on the incidence of cold and flu symptoms, CSC ingestion enhanced proliferation of, and IFN-γ secretion by, γδ T cells challenged in vitro with ethylamine. These findings are consistent with our previous study showing that subjects who drank tea containing L-theanine, but not coffee, increased their γδ T cell function by up to 15-fold [20]. It is important to point out that γδ T cell numbers or serum IFN-γ levels were not increased in subjects taking CSC, but that their γδ T cells were primed in vivo by CSC to respond more vigorously to antigenic challenge. Constitutively increased in γδ T cell numbers and serum IFN-γ titers in the absence of pathogen exposure may actually increase symptoms due to inflammation. Such increased symptoms occur after ingestion of high doses of nitrogen-containing bisphosphonates (which activate γδ T cells) for treatment of osteoporosis [17].

The mechanism of action of symptom reduction has not been determined with certainty. L-theanine is known to activate human γδ T lymphocytes to secrete IFN-γ, a powerful antimicrobial cytokine [19, 20]. Without being bound to any particular mechanistic theory, the inventors proposed that in the early stages of infection, EGCG may aid in the activation of γδ T cells by enhancing secretion of IL-12, a very important factor in γδ T cell activation [20, 18]. If infection does establish itself by evading the first-line γδ T cell response, EGCG may decrease cold and flu symptoms due its anti-inflammatory activity [21]. See also above. Studies in our laboratory are now underway to address these mechanistic questions.

This study has several limitations. Symptom data were collected by self-reporting, so an actual medical diagnosis of cold or flu was not possible. Other illnesses, such as pneumonia, bronchitis, or allergy might have caused similar symptoms. The study was comprised of only healthy adult subjects, so it was not possible to assess the effect of CSC on children, or subjects with chronic illnesses who have increased susceptibility to acute illness.

Cold and flu symptoms can be perennial sources of misery and lost productivity for most healthy adults, and the introduction of a safe, effective, and natural capsule that can prevent such symptoms represents a significant breakthrough in preventive medicine. The foregoing study demonstrates that compositions containing L-theanine in combination with EGCG are a safe and effective preventative for cold and flu symptoms, and for enhancing the innate immune response. Widespread use of CSC could have enormous beneficial effects in decreasing morbidity in healthy populations.

ABBREVIATIONS

CSC, *Camellia sinensis* composition; EGCG, epigallocatechin gallate, PBMC, peripheral blood mononuclear cells

REFERENCES

1. Cabrera C, Artacho R, Gimenez R: Beneficial effects of green tea—a review. J Am Coll Nutr 25(2): 79-99; 2006
2. Chung F L, Schwartz J, Herzog C R, Yang Y M: Proceedings of the third international scientific symposium on tea and human health: Role of flavonoids in the diet. J. Nutr. 33: 3268S-32744S; 2003
3. Chung F L, Schwartz J, Herzog C R, Yang Y M: Tea and cancer prevention: studies in animals and humans. J Nutr 133(10): 3268S-3274S; 2003
4. Michels K B, Willett W C, Fuchs C S, Giovannucci E: Coffee, tea, and caffeine consumption and incidence of colon and rectal cancer. J Natl Cancer Inst 97(4): 282-292; 2005
5. Jordan S J, Purdie D M, Green A C, Webb P M: Coffee, tea and caffeine and risk of epithelial ovarian cancer. Cancer Causes Control 15(4): 359-365; 2004
6. Graham H N: Green tea composition, consumption, and polyphenol chemistry. Preventive Medicine 21(3): 334-350; 1992

7. Nichol K L, D'Heilly S, Ehlinger E: Colds and influenza-like illnesses in university students: impact on health, academic and work performance, and health care use. Clin Infect Dis 40(9): 1263-1270; 2005
8. Eby G A, Halcomb W W: Ineffectiveness of zinc gluconate nasal spray and zinc orotate lozenges in common-cold treatment: a double-blind, placebo-controlled clinical trial. Altern Ther Health Med 12(1): 34-38; 2006
9. Linde K, Barrett B, Wolkart K, Bauer R, Melchart D: Echinacea for preventing and treating the common cold. Cochrane Database Syst Rev (1): CD000530; 2006
10. Das H, Wang L, Kamath A, Bukowski J: Vγ2 and Vδ2 T cell receptor-mediated recognition of aminobisphosphonates. Blood (in press) 2001
11. Nantz M P, Rowe C A, Nieves C, Jr., Percival S S: Immunity and antioxidant capacity in humans is enhanced by consumption of a dried, encapsulated fruit and vegetable juice concentrate. J Nutr 136(10): 2606-2610; 2006
12. Shirai T, Hayakawa H, Akiyama J, et al.: Food allergy to green tea. J Allergy Clin Immunol 112(4): 805-806; 2003
'3. Kim S H, Park H J, Lee C M, et al.: Epigallocatechin-3-gallate protects toluene diisocyanate-induced airway inflammation in a murine model of asthma. FEBS Lett 580(7): 1883-1890; 2006
14. Hisano M, Yamaguchi K, Inoue Y, et al.: Inhibitory effect of catechin against the superantigen staphylococcal enterotoxin B (SEB). Arch Dermatol Res 295(5): 183-189; 2003
15. Wang L, Das H, Kamath A, Bukowski J: Human Vg2Vd2 T cells produce IFN-g and TNF-a with an on/off/on cycling pattern in response to live bacterial products. J. Immunol. 167: 6195-6201; 2001
16. Committee D G A: Dietary guidelines for Americans, 2005. Washington, D.C.: USDA, 2005.
17. Reginster J Y, Adami S, Lakatos P, et al.: Efficacy and tolerability of once-monthly oral ibandronate in postmenopausal osteoporosis: 2 year results from the MOBILE study. Ann Rheum Dis 65(5): 654-661; 2006
18. Katiyar S K: Skin photoprotection by green tea: antioxidant and immunomodulatory effects. Curr Drug Targets Immune Endocr Metabol Disord 3(3): 234-242; 2003
19. Bukowski J F, Morita C T, Brenner M B: Human gd T cells recognize alkylamines derived from microbes, edible plants, and tea: implications for innate immunity. Immunity 11(1): 57-65; 1999
20. Kamath A B, Wang L, Das H, Li L, Reinhold V N, Bukowski J F: Antigens in tea-beverage prime human Vgamma 2Vdelta 2 T cells in vitro and in vivo for memory and nonmemory antibacterial cytokine responses. Proc Natl Acad Sci USA 100(10): 6009-6014; 2003
21. Handa O, Naito Y, Takagi T, et al.: Inhibitory effects of catechins on neutrophil-dependent gastric inflammation. Redox Rep 7(5): 324-328; 2002
22. August D A, Landau J, Caputo D, Hong J, Lee M J, Yang C S: Ingestion of green tea rapidly decreases prostaglandin E2 levels in rectal mucosa in humans. Cancer Epidemiol Biomarkers Prev 8(8): 709-713; 1999
23. Yuan G J, Gong Z J, Sun X M, Zheng S H, Li X: Tea polyphenols inhibit expressions of iNOS and TNF-alpha and prevent lipopolysaccharide-induced liver injury in rats. Hepatobiliary Pancreat Dis Int 5(2): 262-267; 2006
24. Kawai K, Tsuno N H, Kitayama J, et al.: Epigallocatechin gallate attenuates adhesion and migration of CD8+ T cells by binding to CD11b. J Allergy Clin Immunol 113(6): 1211-1217; 2004
25. Singh R, Ahmed S, Malemud C J, Goldberg V M, Haqqi T M: Epigallocatechin-3-gallate selectively inhibits interleukin-1 beta-induced activation of mitogen activated protein kinase subgroup c-Jun N-terminal kinase in human osteoarthritis chondrocytes. J Orthop Res 21(1): 102-109; 2003

TABLE 1

Study withdrawals

| Subject # | Treatment | Capsules Consumed For | Reason for Withdrawal |
|---|---|---|---|
| 2 | CSC | 11 d | Facial & chest rash, itching, red/watery eyes, puffy eyes, congestion) |
| 30 | placebo | ? | Unable to return |
| 43 | CSC | On & off 20 dy (?) | Hives 3x |
| 45 | placebo | 32 dy | Traveling interfered |
| 60 | placebo | 1 mo (?) | Urinary tract infection |
| 116 | placebo | ? | Discontinued taking capsules |
| 119 | placebo | 1 mo (?) | Capsules upsetting stomach |

TABLE 2

Demographics of the study population

| | CSC | Placebo | P value |
|---|---|---|---|
| Age | 28.9 ± 1.07 | 30.3 ± 1.5 | 0.65 |
| Gender male | 20 | 23 | |
| Gender female | 32 | 33 | |
| Height (m) | 1.7 ± 0.01 | 1.7 ± 0.01 | 0.60 |
| Weight (kg) | 74.9 ± 1.7 | 73.3 ± 2.0 | 0.67 |
| BMI | 25.4 ± 0.6 | 24.3 ± 0.8 | 0.94 |
| Compliance (%) | 93% ± 7 | 93% ± 7 | 0.56 |
| Blinding (% guessed correctly) | 50 | 48 | 1.0 |

TABLE 3

Interferon-γ (ng/mL) secreted into the culture medium after 24 h

| | CSC n = 52) | Placebo (n = 56) | p values |
|---|---|---|---|
| 0 mM ethylamine | 2.8$^C$ | 2.3$^C$ | Ethylamine level = 0.001 |
| 1 mM ethylamine | 3.8$^C$ | 2.1$^C$ | Treatment = 0.046 |
| 5 mM ethylamine | 18.4$^A$ | 13.6$^B$ | Interaction = 0.084 |
| Pooled SEM | | 3.9 | |

Repeated measures two-way ANOVA. Means with different superscripts are statistically different using a post hoc SNK test.

TABLE 4

% γδ-T cells in baseline blood sample and after 10 d of culture

| | CSC n = 52) | Placebo (n = 56) | p values |
|---|---|---|---|
| Baseline (no culture) | 13.2 ± 4.6 | 14.3 ± 6.6 | 0.270 |
| 0 ethylamine, 10 d | 20.8 ± 7.0 | 21.9 ± 5.7 | 0.298 |
| 1 mM ethylamine, 10 d | 28.0 ± 5.0 | 20.3 ± 4.0 | 0.017 |

Repeated measures two-way ANOVA; means ± SEM.

TABLE 5

1/56 (1.79%) CSC subjects had diarrhea; 3/55 (5.45%) placebo subjects had diarrhea (67.1%)
3/56 (5.35%) CSC subjects had fever; 7/55 (12.7%) placebo subjects had fever (57.8%)

TABLE 5-continued

This represents the % reduction in subjects experiencing these symptoms, compared to placebo
16/56 (28.6%) CSC subjects had sore throat; 25/55 (45.4%) placebo subjects has sore throat (37.0%)
14/56 (23.2%) CSC subjects had headache; 15/55 (27.2%) placebo subjects had headache (1.47%)
2/56 (3.57%) CSC subjects had nausea; 4/55 (7.27%) placebo subjects had nausea (50.9%)
11/56 (19.6%) CSC subjects had cough; 16/55 (29.1%) placebo subjects had cough (32.6%)
20/56 (35.7%) CSC subject had runny nose; (29/56) (51.8%) placebo subjects had runny nose (31.1%)
19/56 (33.9%) CSC subjects had stuffy nose; 21/55 (38.2%) placebo subjects had stuffy nose (11.2%)

While the principles of the invention have been made clear in illustrative embodiments, there will be immediately apparent to those skilled in the art, in view of the teachings herein, many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

The references referred to herein are incorporated herein in their entirety to the extent they are not inconsistent with the teachings herein.

What is claimed is:

1. A method of reducing symptoms of common cold and/or flu in a subject in need thereof, comprising orally administering a therapeutically amount of an admixture of about 25-300 mg of an L-theanine containing composition, wherein the L-theanine containing composition contains at least 95% L-theanine, and wherein the at least 95% L-theanine is standardized at 99%; and about 50-400 mg of a decaffeinated tea polyphenol composition containing at least 45% epigallocatechin gallate (EGCG), wherein the EGCG is standardized at 50%, wherein said admixture reduces the incidence and/or severity of the symptoms of the common cold and/or flu.

2. The method of claim 1, wherein the admixture is administered in a dosage, wherein the amount of the L-theanine administered is at least 100 mg per day.

3. The method of claim 1, wherein the admixture is administered in a dosage, wherein the amount of the L-theanine administered is at least 150 mg per day and the amount of the EGCG administered is at least 125 mg per day.

4. The method of claim 1, wherein said admixture is disposed in a capsule.

5. The method of claim 4, wherein said admixture is administered as two of said capsules per day.

6. The method of claim 5, wherein said capsules each contain at least 300 mg of said admixture.

* * * * *